US012071410B2

(12) United States Patent
Gupton et al.

(10) Patent No.: US 12,071,410 B2
(45) Date of Patent: Aug. 27, 2024

(54) HIGH-YIELDING CONTINUOUS FLOW SYNTHESIS OF ANTIMALARIAL DRUG HYDROXYCHLOROQUINE

(71) Applicant: VIRGINIA COMMONWEALTH UNIVERSITY, Richmond, VA (US)

(72) Inventors: Frank B. Gupton, Richmond, VA (US); Saeed Ahmad, Chesterfield, VA (US); Hari P. R. Gunuru, Henrico, VA (US); Nakul S. Telang, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 703 days.

(21) Appl. No.: 16/975,434

(22) PCT Filed: Feb. 25, 2019

(86) PCT No.: PCT/US2019/019336
§ 371 (c)(1),
(2) Date: Aug. 25, 2020

(87) PCT Pub. No.: WO2019/165337
PCT Pub. Date: Aug. 29, 2019

(65) Prior Publication Data

US 2020/0407321 A1 Dec. 31, 2020

Related U.S. Application Data

(60) Provisional application No. 62/635,036, filed on Feb. 26, 2018.

(51) Int. Cl.

| | |
|---|---|
| ***C07D 215/46*** | (2006.01) |
| ***B01J 8/04*** | (2006.01) |
| ***B01J 19/00*** | (2006.01) |
| ***B01J 19/18*** | (2006.01) |
| ***B01J 19/24*** | (2006.01) |

(52) U.S. Cl.
CPC .......... *C07D 215/46* (2013.01); *B01J 8/0492* (2013.01); *B01J 19/0013* (2013.01); *B01J 19/0066* (2013.01); *B01J 19/1862* (2013.01); *B01J 19/245* (2013.01); *B01J 2219/00033* (2013.01); *B01J 2219/0004* (2013.01)

(58) Field of Classification Search
CPC ... C07D 215/46; B01J 8/0492; B01J 19/0013; B01J 19/0066; B01J 19/1862; B01J 19/245; B01J 2219/00033; B01J 2219/0004
See application file for complete search history.

(56) References Cited

U.S. PATENT DOCUMENTS 2,546,658 A 3/1951 Surrey et al.

FOREIGN PATENT DOCUMENTS

| | | | |
|---|---|---|---|
| WO | 2005/062723 | * | 7/2005 |
| WO | 2005/062723 | A2 | 7/2005 |
| WO | 2010/027150 | A2 | 3/2010 |
| WO | 104803859 | A | 7/2015 |

OTHER PUBLICATIONS

Yu, Beilstein J Org Chem, 2018, vol. 14, 583-592. (Year: 2018).*

* cited by examiner

*Primary Examiner* — D Margaret M Seaman
(74) *Attorney, Agent, or Firm* — WC&F IP

(57) ABSTRACT

Cost effective, semi-continuous flow methods and systems for synthesizing the antimalarial drug hydroxychloroquine (HCQ) in high yield are provided. The synthesis method that uses simple, inexpensive reagents to obtain the crucial intermediate 5-(ethyl(2-hydroxyethyl)-amino)pentan-2-one, vertical-integration of the starting material 5-iodopentan-2-one and the integration of continuous stirred tank reactors.

19 Claims, 9 Drawing Sheets

Hydroxychloroquine
(1)

Chloroquine
(2)

3 4 5 6

3 7 6

HCQ (1)

12

11

6

10

8

HIGH-YIELDING CONTINUOUS FLOW SYNTHESIS OF ANTIMALARIAL DRUG HYDROXYCHLOROQUINE

STATEMENT OF FEDERALLY SPONSORED RESEARCH AND DEVELOPMENT

This invention was made with government support under contract W911NF-16-2-0023 awarded by the Defense Advanced Research Projects Agency (DARPA). The United States government has certain rights in the invention.

BACKGROUND OF THE INVENTION

Field of the Invention

The invention generally relates to improved, cost effective, semi-continuous flow systems and methods for synthesizing hydroxychloroquine (HCQ). In particular, the invention provides a synthesis method that uses simple, inexpensive reagents to obtain the crucial intermediate 5-(ethyl(2-hydroxyethyl)amino)pentan-2-one, vertical-integration of the starting material 5-iodopentan-2-one, and the integration of continuous stirred tank reactors (CSTRs).

Description of Related Art

In 2016, an estimated 212 million cases of malaria, including 429,000 fatalities, were reported worldwide, with the majority of these cases occurring in sub-Saharan Africa and Southern Asia. The malaria epidemic is particularly difficult to control due to the multi-drug resistant nature of the malaria parasite *Plasmodium falciparum*.

Hydroxychloroquine (FIG. 1A, HCQ) is an anti-malarial drug developed for both treatment and prevention of the disease in response to the widespread malaria resistance to chloroquine, (FIG. 1B, CQ). The World Health Organization has identified HCQ as an essential anti-malarial medication for a basic healthcare system. Additionally, hydroxychloroquine (HCQ) is an effective non-steroidal anti-inflammatory drug in the treatment of various autoimmune diseases such as rheumatoid arthritis (e.g. in cardiovascular patients), lupus, and childhood arthritis (or juvenile idiopathic arthritis) among others. Unfortunately, global access to HCQ has been hindered by high manufacturing costs. Thus, the development of cost effective synthetic strategies to increase global access to this important global health drug is of great importance.

The current HCQ commercial synthesis employs the key intermediate 5-(ethyl(2-hydroxyethyl) amino)pentan-2-one, 6, and its production is a major cost driver (see FIG. 2A). An alternative route (FIG. 2B) by Li and co-workers (2015) eliminates the protection-deprotection steps, but its use of a complex multi transition metal catalyst system to achieve direct $S_N2$ substitution of the chlorine on 3 by the amine 7, is sub-optimal.

There is a pressing need to develop new methods of synthesizing HCQ that are cost effective while producing the drug in high yield.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Provided herein is a cost effective semi-continuous flow method for the synthesis of the antimalarial drug HCQ. The synthesis involves the reaction of simple, inexpensive reagents to obtain crucial intermediates for the reaction, and overall employs a reduced number of synthesis steps while achieving a high, multi gram yield of the product. The synthetic strategy involves vertical-integration of the starting material 5-iodopentan-2-one and the integration of continuous stirred tank reactors for key steps of the method.

It is an object of this invention to provide a method for synthesizing hydroxychloroquine (HCQ), comprising: in a flow reactor, i) reacting 5-iodopentan-2-one with 2-(ethylamino)ethan-1-ol to form 5-(ethyl(2-hydroxyethyl)amino) pentan-2-one; and ii) converting 5-(ethyl(2-hydroxyethyl) amino)pentan-2-one to (E)-5-(ethyl(2-hydroxyethyl)amino) pentan-2-one oxime; and in a first continuous stirred tank reactor (CSTR) iii) contacting (E)-5-(ethyl(2-hydroxyethyl) amino)pentan-2-one oxime with a catalyst to form 5-(ethyl (2-hydroxyethyl)amino)-2-aminopentane; and in a second CSTR, iv) reacting the 5-(ethyl(2-hydroxyethyl)amino)-2-aminopentane with 4,7,-dichloroquinoline in the presence of a base to form HCQ. In some aspects, steps i), ii) and iii) are conducted in a solvent that is the same for each step. In additional aspects, the solvent is tetrahydrofuran (THF). In other aspects, reacting step iv) is performed in an alcohol. In further aspects, the alcohol is ethanol. In yet further aspects, the base is $K_2CO_3/Et_3N$. In other aspects, reacting step iv) proceeds for 6 hours. In additional aspects, the 5-iodopentan-2-one is formed by a) reacting α-acetyl butyrolactone with an iodine donor in an aqueous solvent. In yet further aspects, the method further comprises a step of b) extracting the 5-iodopentan-2-one from the aqueous solvent with an organic solvent. In additional aspects, the steps of a) reacting and b) extracting are performed in line in a first flow reactor. In other aspects, the first flow reactor is in line with the flow reactor of claim 1. In further aspects, the iodine donor is hydroiodic (HI) acid. In yet further aspects, the α-acetyl butyrolactone is neat. In additional aspects, the step of extracting is performed using a hydrophobic, membrane-based separator. In further aspects, the catalyst is a Raney nickel catalyst.

The disclosure also provides a system for synthesizing hydroxychloroquine (HCQ), comprising a first heated reactor coil configured to receive 5-iodopentan-2-one and 2-(ethylamino)ethan-1-ol and output 5-(ethyl(2-hydroxyethyl) amino)pentan-2-one; a first packed bed reactor comprising a neutralizing agent and configured to receive 5-(ethyl(2-hydroxyethyl)amino)pentan-2-one from the first heated reactor and output neutralized 5-(ethyl(2-hydroxyethyl) amino)pentan-2-one; a second heated reactor coil configured to receive neutralized 5-(ethyl(2-hydroxyethyl)amino)pentan-2-one from the first packed bed reactor, receive hydroxylamine, and output (E)-5-(ethyl(2-hydroxyethyl) amino) pentan-2-one oxime; a second packed bed reactor comprising a neutralizing agent and configured to receive 5-(ethyl(2-hydroxyethyl)amino)pentan-2-one oxime from the second heated reactor coil, and output neutralized (E)-5-(ethyl(2-hydroxyethyl)amino)pentan-2-one oxime; a first continuous stirred tank reactor (CSTR) configured to contain a catalyst, receive neutralized (E)-5-(ethyl(2-hydroxyethyl) amino) pentan-2-one oxime from the second packed bed reactor, and output 5-(ethyl(2-hydroxyethyl)amino)-2-aminopentane; and a second CSTR configured to receive 5-(ethyl(2-hydroxyethyl)amino)-2-aminopentane from the first CSTR, receive 4,7,-dichloroquinoline, and output HCQ. In certain aspects, the system further comprises a heated reaction coil configured to receive α-acetyl butyrolactone and receive an iodine donor, and output 5-iodopentan-2-one, a reaction coil configured to receive 5-iodopentan-2-one from the heated reaction coil, and receive a base and a hydrophobic, membrane-based separator configured to receive 5-iodopentan-2-one from the unheated reaction coil extract 5-iodopentan-2-one from the aqueous solvent with an organic solvent, and output 5-iodopentan-2-one in an organic phase. In additional aspects, the first heated reactor coil receives the 5-iodopentan-2-one in an organic phase from the hydrophobic, membrane-based separator. In yet further aspects, the catalyst is a Raney nickel catalyst.

DETAILED DESCRIPTION

Figure 1A:
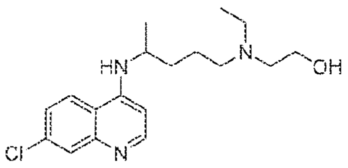
FIGS. 1A and B. Commercially available antimalarial drugs. A, hydroxychloroquine (HCQ); B, chloroquine (CQ).
Figure 1B:
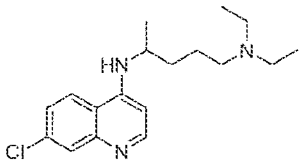

Provided herein is a highly efficient method for the semi-continuous synthesis of the antimalarial drug hydroxychloroquine (HCQ). The method is "semi-continuous" because some steps of the method are conducted using continuous flow but others are conducted using continuous stirred tank reactors (CSTR) which are vertically integrated into the process. The method results in an overall yield improvement of about 52% over the current commercial HCQ production process, even though the methods use reactants that are simpler and less expensive than those employed in current commercial processes. A key feature in the new process is the elimination of protecting groups without invoking the use of expensive catalysts as required by Li (2015). The present high-yielding, multigram-scale semi-continuous synthesis thus provides an opportunity to achieve increased affordable global access to hydroxychloroquine for the prevention and treatment of malaria and various autoimmune diseases.

The reactions of the continuous flow method are preferably carried out using the same solvent for several steps; however, this is not necessarily always the case. Those of skill in the art may choose to separate one or more of the optimized steps of the method and/or to use a different solvent or multiple solvents (e.g. rinsing the lines with the appropriate solvent prior to use), to make HCQ. Alternatively, one or more of the optimized reactions, either individually or in groups of several reactions, may be used for purposes other than making HCQ. For example, the starting materials and intermediates described herein are useful chemicals for a variety of purposes, and may be of interest in and of themselves, without further conversion. All such methods of making each chemical entity disclosed herein are encompassed.

Definitions

Raney nickel catalyst: Raney nickel is a fine-grained solid composed mostly of nickel derived from a nickel-aluminum alloy. Several grades are known, but most are gray solids. Some are pyrophoric, most are used as air-stable slurries. The original form, Raney®-Nickel is a registered trademark of W. R. Grace and Company, but other generic forms are known and are also referred to generically as "Raney nickel" or as e.g. "skeletal catalyst" or "sponge-metal catalyst". These catalysts have properties similar to those of Raney®-Nickel. The catalyst may be a binary Ni—Al alloy and/or may comprise small amounts of a third metal (a "promoter") such as zinc or chromium, forming a ternary alloy. The third metal enhances the activity of the catalyst. All forms of this catalyst may be used in the methods described herein. Continuous stirred-tank reactors (CSTR), also known as vat- or backmix reactors, or continuous-flow stirred-tank reactors (CFSTR), are known in the art. CSTRs facilitate rapid dilution rates which make them resistant to both high pH and low pH fluctuations. It is sometimes economically beneficial to operate several CSTRs in series, e.g. for the same reaction, and this strategy may be implemented in the present methods. This allows, for example, the first CSTR to operate at a higher reagent concentration and therefore a higher reaction rate. In these cases, the sizes of the reactors may be varied in order to minimize the total capital investment required to implement the process.

Room temperature generally refers to a temperature of from about 15-25° C., and is generally about 20-22° C.

Reactions

Synthesis of Starting Material (10)

Figure 2A:
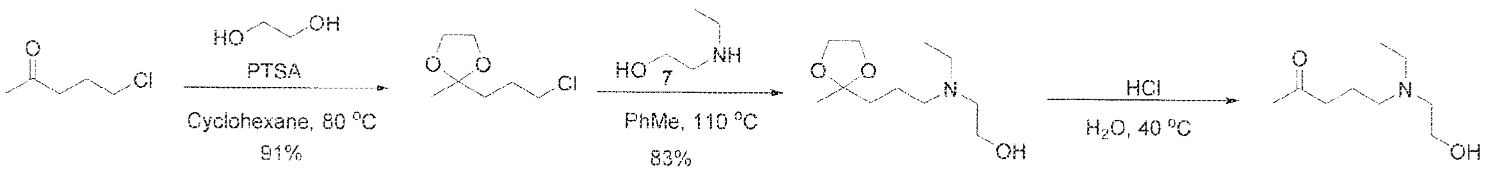
FIGS. 2A and B. Batch Syntheses of 5-(ethyl(2-hydroxyethyl) amino)pentan-2-one. A, prior art method; B, prior art method of Li (2015).
Figure 2B:
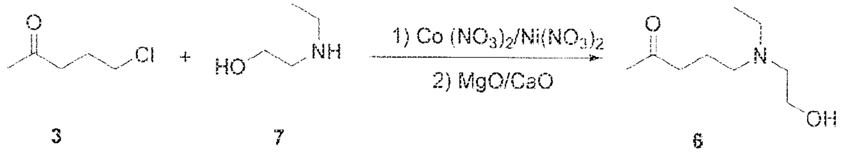
Figure 4:
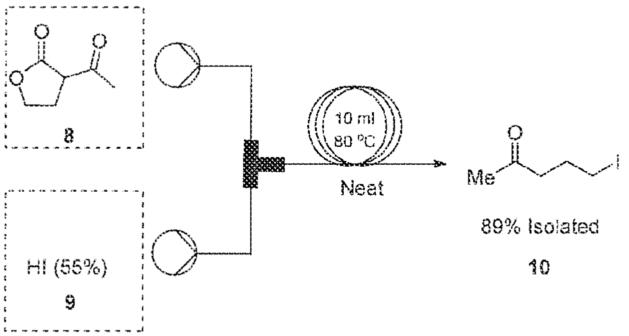
FIG. 4. Flow process for synthesis of 5-iodopentan-2-one (10).

In the present synthesis, 5-iodopentan-2-one (10) replaces the traditional chlorinated starting material (3 in FIG. 2). This iodinated starting material is made using α-acetyl butyrolactone 8 (used neat) via a decarboxylative ring-opening reaction, generally via reaction with an aqueous solution of an iodine donor (e.g. see FIG. 4). Iodine donors that may be used include but are not limited to e.g. HI, FI, NaI, KI, LiI, etc. In some aspects, the iodine donor is HI in an aqueous solution. The amount of iodine donor (e.g. HI) is typically at least about 20 to about 60%, and is generally at least about 40%, and is preferably at least about 50%, such as about 55%. The temperature of the reaction is generally at least about 40° C. or above, e.g. about 40, 45, 50, 55, 60, 65, 70, 75, 80, 85 or 90° C., with about 80° C. being a preferred temperature. The reaction optimally proceeds for about 2.5 to about 15 minutes, e.g. about 2.5, 5.0, 10.0, or 15.0 minutes or longer, with about 5-10 minutes being the preferred range, e.g. about 5, 6, 7, 8, 9, or 10 minutes. The reaction pressure is generally from about 1.5 to 5.0 bar, e.g. about 1.5, 2.0, 3.0, 3.5, 4.0, 4.5 or 5.0 bar, with about 3 bar being preferred. The reaction can optionally be monitored, e.g. by GC-MS, $^{1}$H NMR, etc. No intermediates are produced and the starting material is completely consumed during the reaction.

Figure 5:
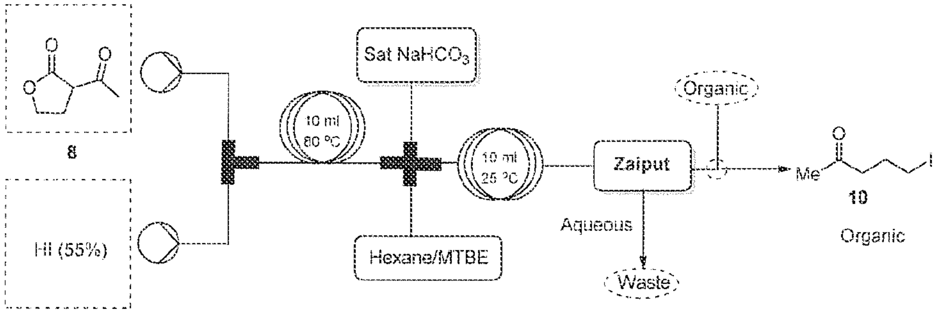
FIG. 5. Schematic representation for continuous in-line extraction of 10.

In preferred aspects, extraction and neutralization are accomplished in-line as part of a flow-based method as shown in FIG. 5. An amphoteric compound which functions as a base (such as saturated sodium bicarbonate ($NaHCO_3$) or $Na_2CO_3$, (sodium carbonate), potassium carbonate ($K_2CO_3$), etc.,) and one or more suitable organic solvents (e.g. hexanes and/or methyl tert-butyl ether, methylene chloride (DCM), ethyl acetate, etc.) are introduced in-line and are reacted with 5-iodopentan-2-one (10) in a reactor coil maintained at room temperature (e.g. about 25° C.). One or more hydrophobic, membrane-based separators receive the input from the reactor coil and it is used to produce an aqueous waste stream (comprising excess HI) and an organic stream comprising 10. Examples of suitable hydrophobic, membrane-based separators include but are not limited to: Zaiput, Versapore®, Zefluor™, polytetrafluoroethylene (PTFE), polycarbonate membrane, etc. When a membrane-based separator is used, there is a loss of product to the water layer (e.g. generally 10% or less) but this is tolerated in order to avoid the need for complete batch workup steps.

Figure 6:
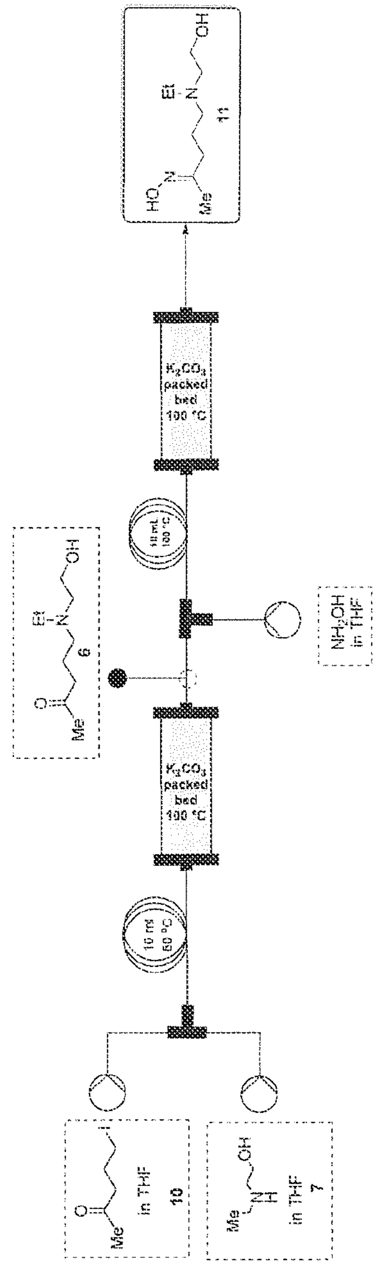
FIG. 6. Schematic representation of continuous telescoped process to synthesize 11.
Figure 7:
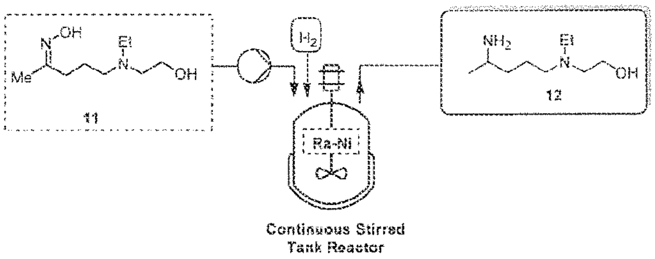
FIG. 7. Schematic representation of reductive amination of 12.

In some aspects, 10 is then transferred (integrated) directly into a flow method, e.g. as the input to the next reactor coil, depicted in FIG. 6. Alternatively, the reaction and separation may be done in batch in which crude 10 is extracted (generally at room temperature) e.g. with one or more hydrophobic solvents (as listed above), and neutralized e.g. to about pH=7 using a base (as listed above). The combined organic phases are dried (e.g. using anhydrous sodium sulfate) and evaporated in vacuo to dryness to yield 10 for use in the first step of the semi-continuous synthesis method described in detail below.

Steps of the Reaction to Form HCQ

Synthesis of 5-(ethyl(2-hydroxyethyl)amino)pentan-2-one (6)

5-iodopentan-2-one (10) formed as described above is used to synthesize 5-(ethyl(2-hydroxyethyl)amino)pentan-2-one (6) as follows:

Compound 6 is synthesized from 10 in a flow reactor unit, preferably using a solvent system that is compatible with subsequent flow reactions of the method. In some aspects, the solvent is tetrahydrofuran (THF). However, other solvents such as 1,4-dioxane, 2-methyl THF (tetrahydrofuran), MTBE (methyl tert-butyl ether), DCM (dichloromethane or methylene chloride), etc., may also be employed. Those of skill in the art will recognize the advantages of rinsing the flow reactor with dry solvent and/or flushing the system with an inert gas (e.g. $N_2$) prior to use.

To perform the reaction, 10 is combined with 2-(ethylamino)ethan-1-ol (7) in a suitable solvent, e.g. THF at about room temperature and streamed into a reactor coil, as depicted in FIG. 6. The temperature in the coil is in the range of from about 70 to 90° C., e.g. about 70, 95, 80, 85 or 90° C., and the flow rate typically ranges from about 0.1 to about 1.0 ml/min, e.g. about 0.1, 0.2, 0.3, 0.4, 0.5, 0.6, 0.7, 0.8, 0.9 or 1.0 ml/min or higher, for larger coils.

The reaction is then quenched by passing the reaction mixture e.g. through a packed bed reactor containing e.g. potassium carbonate, sodium carbonate, lithium carbonate, lithium hydroxide, sodium bicarbonate, or other suitable material. The temperature in the packed bed reactor is generally about 85-100° C., such as about 85, 90, 95 or 100° C. This yields product 6, which is transferred directly to the next in-line step.

Alternatively, the output of the reaction between 10 and 7 is collected and quenched, extracted with one or more organic solvents (e.g. DCM) and the combined organic layers are dried over sodium sulfate, and evaporated to give 6, which can be used in further reactions.

Synthesis of (E)-5-(ethyl(2-hydroxyethyl)amino) pentan-2-one oxime (11)

Compound 6 is ultimately converted to 5-(ethyl(2-hydroxyethyl)amino)-2-aminopentane 12 via intermediate oxime 11. Briefly, a simple conversion of the ketone group of 6 yields oxime 11, which is then reduced to give 12.

A. Synthesis of Oxime 11

The conversion of 6 to oxime 11 is preferably done in-line as part of a continuous flow synthesis method, as shown in FIG. 6. 6 is combined with an agent such as $NH_2OH$ (e.g. about 0.5, 1.0 or 1.5 M). This reaction is generally performed in a reactor coil (e.g. at about 0.5, 1.0 or 1.5 mL/min, such as about 1.0 mL/min) at a temperature of from about 80 to 100° C., e.g. about 80, 85, 90, 95 or 100° C., and with a tR of about 15-30 minutes, e.g. about 15, 20, 25, or 30 minutes such as about 20 min. The reaction is quenched e.g. by passage through a packed bed reactor comprising a compound such as potassium carbonate, sodium carbonate, lithium carbonate, lithium hydroxide, sodium bicarbonate, etc. The temperature in the packed bed reactor is generally about 85-100° C., such as about 85, 90, 95 or 100° C. This yields oxime 11.

If needed, 11 is e.g. concentrated, taken up in a solvent such as DCM, etc. prior to the next reaction. However, further purification is generally not needed and 11 may pass directly to the next step.

Synthesis of 5-(ethyl(2-hydroxyethyl)amino)-2-aminopentane (12)

The next to last step of the production of HCQ is the conversion of oxime 11 to 5-(ethyl(2-hydroxyethyl)amino)-2-aminopentane (12). Accordingly, product 11 is passed to the next reaction, which takes place in a continuous stirred tank reactor (CSTR). 11 is efficiently reduced to 12 in a CSTR using a suitable solvent (e.g. THF, diglyme, 1,4-dioxane, methanol, ethanol, 2-methyl THF, IPA (2-propanol)), etc. Significantly, the reaction proceeds in the presence of a Raney Nickel catalyst, which is retained or sequestered in the CSTR. The reaction mixture comprises compound 11 at a concentration ranging from about 0.05-2.0 M (such as about 0.05, 0.1, 0.2, 0.3, 0.4, 0.5. 0.6, 0.7, 0.8, 0.9, 1.0, 1.1, 1.2, 1.3, 1.4, 1.5, 1.6, 1.7, 1.8, 1.9, or 2.0, in a suitable solvent. The solvent is preferably the same as that which is used in the previous flow steps, such as THF or diglyme, 1,4-dioxane, methanol, ethanol, 2-methyl THF, IPA, etc. However, this is not strictly necessary and methods which use other solvents for one or more steps of the method are also encompassed. The reaction mixture is generally introduced into the reaction vessel at a set flow rate of e.g. 0.6-2.5 mL $min^{-1}$, such as about 0.6, 1.0, 1.5, 2.0 or 2.5 mL $min^{-1}$. The reaction pressure is typically set to about 5-15 bar, such as about 10 bar with an inert gas such as hydrogen supplied at a suitable flow rate (e.g. 0.1 to 1.0 mL min¯1, such as about 0.5 mL $min^{-1}$). The reaction takes place at a temperature in the range of from about 70 to about 90° C., e.g. about 70, 75, 80, 85 or 90° C. such as about 80° C. The reaction generally proceeds with agitation, e.g. stirring (e.g. at about 500 to 100 rpm, such as about 750 rpm) to provide proper mixing. The reaction volume may be monitored and when suitable (e.g. when a difference between two thermocouples is detected, such as about a 1, 2, 3, 4, or 5° C. difference, such as a 3° C. difference), a level control opens, allowing products to exit the reactor. Conversely, when the temperature difference between the two thermocouples is greater than e.g. about 1, 2, 3, 4, or 5° C., such as 3° C., reactants enter the tank. Product is collected e.g. when a steady-state is reached. The reaction mixture is (optionally) filtered and/or dried, extracted, etc., prior to being used in the next (and last) step of the reaction.

Synthesis of Hydroxychloroquine (1)

The final step in the synthesis of HCQ involves the reaction of 12 with 4,7,-dichloroquinoline, 13. This step is also performed in a CSTR, and the reactions take place in an alcohol solvent, preferably ethanol. However, in some aspects, other alcohols such as methanol, n-butanol, isopropanol, etc. may be employed. The reactants are 12 plus a suitable base, e.g. NaOH, KOH, $K_2CO_3$, $ET_3N$, DIPEA (N,N-Diisopropylethylamine), or combinations thereof, especially combinations with $ET_3N$ such as NaOH/$ET_3N$, DIPEA/$ET_3N$ or $K_2CO_3$/$ET_3N$. In preferred aspects, $K_2CO_3$/$Et_3N$ is used. This step is advantageously accelerated (compared to conventional methods) by employing $K_2CO_3$/$Et_3N$. As a result, a high yield of HCQ is obtained, e.g. in less than about 6 hours of reaction time.

Reactants, 13 and 12 are combined in approximately a 1/1 molar ratio (e.g. about 1/1.2 molar ratio, respectively) with equal equivalents of $Et_3N$ and $K_2CO_3$. The amount of each of $Et_3N$ and $K_2CO_3$ is generally about half that that of reactant 13, mole/mole. The reactants are combined in sufficient solvent e.g. ethanol to allow thorough mixing. The reaction is allowed to proceed in an inert atmosphere (e.g. under $N_2$) at a temperature of about 100 to 150° C., e.g. at about 100, 105, 110, 115, 120, 125, 130, 135, 140, 145 or 150° C., such as about 125° C., and requires about 6 hours for completion.

Following completion of the reaction, ethanol is removed (e.g. via distillation) and the product is recovered e.g. by extraction, separation, drying, etc. as needed to afford the final product.

Systems

Also provided are systems for synthesizing hydroxychloroquine (HCQ). The systems are semi-continuous flow systems and comprise elements/components that are in-line, flow components and also CSTRs. For example, the systems generally comprise a plurality of reaction coils (also referred to herein as "reactor coils"), e.g. generally 3 or 4, which may or may not be heated, depending on the reaction(s) that take place within a coil. The systems also generally comprise a plurality of packed bed reactors. In addition, various lines, valves, connectors, separators, reservoirs (e.g. to serve as sources of a reactant), etc. are included in the system, and the system components are advantageously operably linked in-line. That is to say, generally a product, such as a reactant, that is produced in one component of the system is transferred directly to a component in which it undergoes a further reaction, without intervening steps of purification (other than e.g. steps of phase separation, neutralization, etc. which can also be done in-line).

In some aspects, the systems comprise a first heated reactor coil that is configured to (i.e. comprises a least one inlet to) receive 5-iodopentan-2-one and 2-(ethylamino) ethan-1-ol, and an outlet to output 5-(ethyl(2-hydroxyethyl) amino)pentan-2-one, usually directly into a first packed bed reactor. The first packed bed reactor typically comprises a neutralizing agent and is configured to include an inlet to receive input from first heated reactor coil, typically 5-(ethyl (2-hydroxyethyl)amino)pentan-2-one. The 5-(ethyl(2-hydroxyethyl)amino) pentan-2-one flows through the first packed bed reactor, is neutralized, and is then passed directly to a second heated reactor coil configured to (having at least one inlet to) receive neutralized 5-(ethyl(2-hydroxyethyl) amino)pentan-2-one from the first packed bed reactor. The second heated coil is also configured to receive hydroxylamine, and a reaction takes place in the second heated coil to form (E)-5-(ethyl(2-hydroxyethyl)amino)pentan-2-one oxime. The oxime is output from the second heated reaction coil to a second packed bed reactor, which like the first packed bed reactor, comprises a neutralizing agent. The neutralizing agents in the first and second packed bed reactors may be the same or different. The second packed bed reactor comprises an inlet to receive 5-(ethyl(2-hydroxyethyl)amino)pentan-2-one oxime from the second heated reactor coil and outlet to output neutralized (E)-5-(ethyl(2-hydroxyethyl)amino)pentan-2-one oxime.

The systems disclosed herein also comprise one or more continuous stirred tank reactors (CSTRs) which comprise a stirring mechanism. For example, a first CSTR is generally configured to contain a Raney nickel catalyst, receive neutralized (E)-5-(ethyl(2-hydroxyethyl)amino) pentan-2-one oxime from the second packed bed reactor, and output 5-(ethyl(2-hydroxyethyl)amino)-2-aminopentane. This CSTR generally also comprises an inlet for a gas, e.g. an inert gas such as $H_2$. Typically the output of the first CSTR is received by a second CSTR. The second CSTR receives both 5-(ethyl(2-hydroxyethyl)amino)-2-aminopentane (from the first CSTR) and 4,7,-dichloroquinoline (from a source of 4,7,-dichloroquinoline). The reaction between these two chemicals within the second CSTR produces HCQ, which can subsequently be output from the second CSTR for further processing, if needed (e.g. via extraction, purification, concentration, drying, etc. Further processing generally also includes forming the HCQ into dosage forms, e.g. tablets, liquid dosage forms, etc.

Is some aspects, the 5-iodopentan-2-one that is input into the first reaction coil is transferred from another in-line flow system, which may be integrated directly into the system described above, or may be a stand-alone system. This second system comprises at least a heated reaction coil configured to receive α-acetyl butyrolactone and an iodine donor. The reaction that takes place in the heated reaction coil produces 5-iodopentan-2-one, which is then output to a reaction coil configured to receive the 5-iodopentan-2-one from the heated reaction coil, and also to receive a base. The reaction coil may or may not be heated because the reaction takes place, e.g. at room temperature (rt). However, in some aspects, heating may be required to maintain the reaction coil at a consistent temperature, e.g. at or near rt.

This segment of the overall system further comprises at least one hydrophobic, membrane-based separator with an inlet to receive 5-iodopentan-2-one from the rt reaction coil. The hydrophobic, membrane-based separator extracts 5-iodopentan-2-one into an organic solvent, and outputs the 5-iodopentan-2-one in an organic phase via a suitable outlet. In some aspects, the 5-iodopentan-2-one is transferred directly in-line into the first heated reactor coil described above, e.g. without intervening steps of collection, purification, etc. In other aspects, the 5-iodopentan-2-one is collected and processed as needed, before being provided as the starting material in the semi-continuous system described above, e.g. before being input into the first reaction coil.

Figure 9:
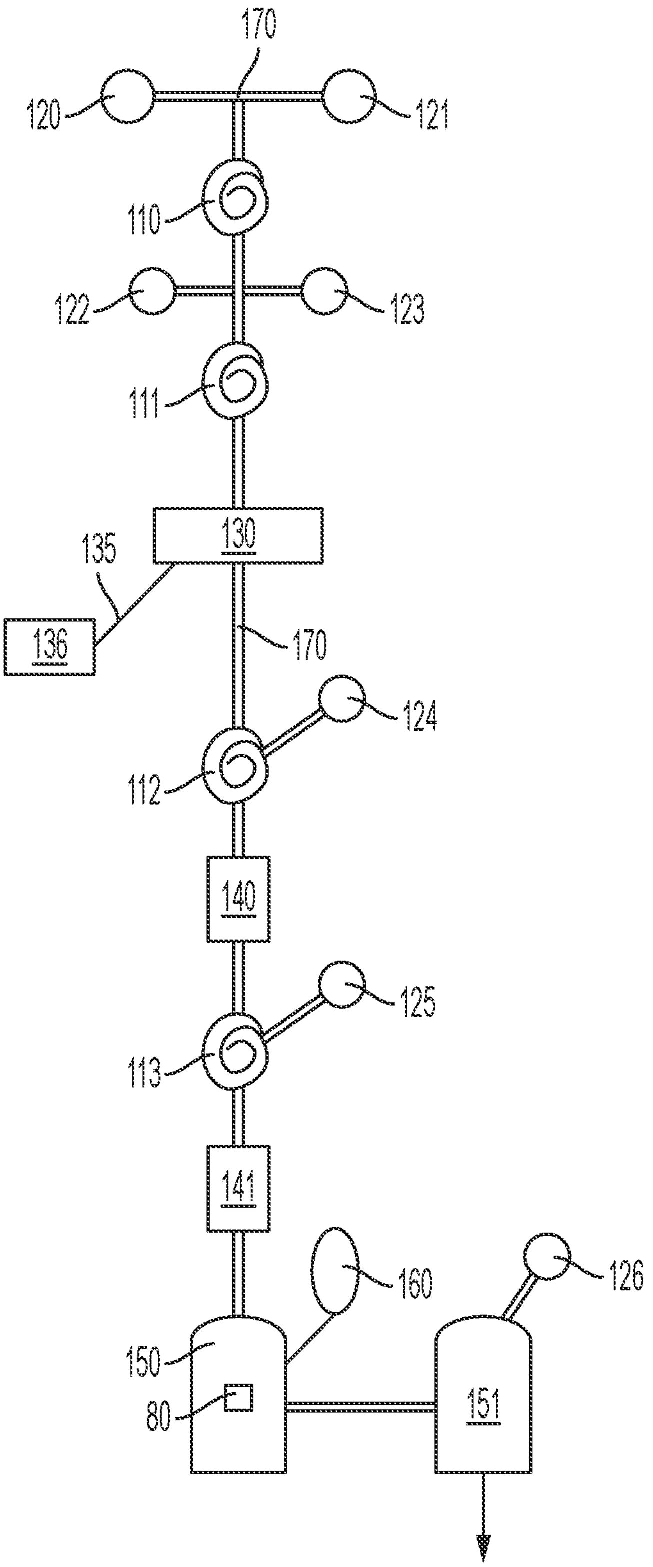
FIG. 9. Schematic representation of a flow system.

A schematic, non-limiting representation of an exemplary semi-continuous flow system is shown in FIG. 9. Depicted are multiple reaction coils 110, 111, 112 and 113; multiple reservoirs (120, 121, 122, 123 and 124) for containing/storing reactants which are supplied to other components via connecting lines (170), valves (not depicted), etc., a hydrophobic membrane separator 130 from which waste passes through waste line 135 to waste container 136, multiple bed reactors 140 and 141, two CSTRs 150 and 151, and a gas storage tank 160. In the exemplary system that is shown:

- reactants α-acetyl butyrolactone (8) and an iodine donor flow from reservoirs 120 and 121, respectively;
- starting material 5-iodopentan-2-one (10) is produced in reaction coil 110 and flows to reaction coil 111 as do e.g. hexane/MTBE and $NaHCO_3$ (from reservoirs 122 and 123, respectively);
- 5-iodopentan-2-one (10) and the reaction milieu enter hydrophobic membrane separator 130;
- 5-iodopentan-2-one (10) in an organic phase flows from membrane separator 130 to reaction coil 12 while aqueous waste flows to waste container 136 via waste line 135;
- 2-(ethylamino)ethan-1-ol (7) is introduced to reaction coil 112 from reservoir 124;
- 5-(ethyl(2-hydroxyethyl)amino)pentan-2-one (6) is produced in reaction coil 112 and enters packed bed reactor 140, where the reaction is quenched;
- 5-(ethyl(2-hydroxyethyl)amino)pentan-2-one (6) enters reaction coil 113 together with a base from reservoir 125;
- (E)-5-(ethyl(2-hydroxyethyl)amino)pentan-2-one oxime (11) is produced in reaction coil 113 and then passes through packed bed reactor 141 and then to CSTR 150;
- 5-(ethyl(2-hydroxyethyl)amino)-2-aminopentane (12) is synthesized in CSTR 150 (e.g. containing Raney nickel catalyst 80 and under $H_2$ gas from gas storage tank 160) and passes to CSTR 151; and
- 4,7,-dichloroquinoline, 13 enters CSTR from reservoir 126, and the final product, HCQ is synthesized in CSTR 116.

The arrow leaving CSTR 151 illustrates removal of HCQ.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLE

Figure 3:
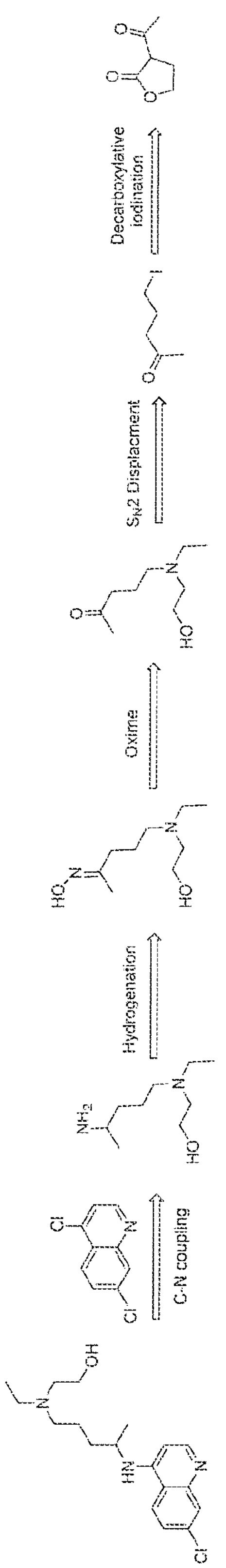
FIG. 3. Retrosynthetic strategy to hydroxychloroquine.

The continuous synthesis described herein involves a retrosynthetic process (FIG. 3) in which 10, an iodo analogue to starting material 3, is generated in a single step via a decarboxylative ring-opening of α-acetyl butyrolactone 8. The iodo-analogue, 10, is then used without isolation to prepare compound 6.

A direct one-step reductive amination of 6 to give 12 can be accomplished by simple heterogeneous reduction with $H_2$/Raney-Nickel. However, THF is employed in all of the prior flow steps and is a poor choice as a solvent for the reductive amination step due to limited solubility of ammonia in THF. $H_2$/Raney-Nickel reductions are often carried out in alcoholic media where much higher concentrations of ammonia are achievable but would require a solvent exchange. There are many reports of continuous flow chemistry methods for reductive amination of ketones [25-31]; however, such processes typically require soluble reductants such as diisobutylaluminium hydride (DIBAL-H), superhydrides, or supported borohydride species [32-36]. Although these approaches are effective, they are significantly more costly than using simple heterogeneous reduction with $H_2$/Raney-Nickel. Therefore, we explored an alternate strategy: first, simple conversion of the ketone group of 6 to oxime 11, which is then followed by reduction with $H_2$/Raney-Nickel to give 5-(ethyl(2-hydroxyethyl)amino)-2-aminopentane 12. This efficiently reduces 11 to 12 with THF as the solvent in a continuous stirred tank reactor (CSTR).

The last step of HCQ synthesis requires reaction of 12 with 4,7,-dichloroquinoline, 13, which when used neat takes 24-48 hours at 120-140° C. to give 75-80% yield of HCQ, 1 [37]. We have found that this step can be accelerated by employing $K_2CO_3$/triethylamine, to facilitate the formation of HCQ, 1, resulting in a comparable yield in less than 6 hours. Thus, we have integrated the continuous preparation of reaction with a new efficient continuous flow synthesis of 12 with the final step by using a CSTR to accommodate the longer reaction time required to produce HCQ.

Initial optimization efforts to prepare 6 revealed poor reactivity of starting material 3, so we pursued the iodo-analogue of 3, 5-iodopentan-2-one (10) as an alternative. By optimizing the reaction concentration, we have also shown that 10 reacts rapidly and cleanly with 7 under flow conditions to give 6 in high-yield (>80%). Furthermore, we have developed and optimized a continuous synthesis of 10 (Table 1, (FIG. 4), wherein hydroiodic acid is reacted with neat 3-acetyldihydrofuran-2(3H)-one, 8, to provide a rapid route to 10 which is significantly higher in yield than previously reported syntheses [38-39]. Initial results using diluted hydroiodic acid (20-40%) provided only modest conversion to product over a range of temperatures (Table 1, entries 1-5); however, use of 55% hydroiodic acid (Table 1, entries 6-8) was found to give near quantitative conversion. The reaction profile was monitored using GC-MS and $^1H$ NMR—no intermediates were observed under these conditions. Optimization of the flow rate with 55% hydroiodic acid (Table 1, entries 6-8) revealed that a flow rate of 1.0 ml ($t_R$=5 min) gave an isolated yield of 89%.

TABLE 1

Optimization of the Flow Process for Synthesis of 10

| Entry | HI [Aqueous %] | Temp (° C.) | $t_R$ = min | Pressure (bar) | Conv [a] (%) |
|---|---|---|---|---|---|
| 1 | 20 | r.t. | 5 | 1.5 | 5 |
| 2 | 20 | 40 | 5 | 2.0 | 31 |
| 3 | 20 | 80 | 5 | 2.0 | 34 |
| 4 | 40 | 80 | 5 | 2.0 | 43 |
| 5 | 40 | 80 | 5 | 2.5 | 46 |
| 6 | 55 | 80 | 5 | 3.0 | 98 (89%)[b] |
| 7 | 55 | 80 | 2.5 | 3.0 | 91 |
| 8 | 55 | 80 | 10 | 3.0 | 92 |

[a] conversion determined by GC-MS and $^1H$ NMR
[b]Isolated yield

Due to the need to use an excess of hydroiodic acid it is important to remove its excess from the eluting reaction stream before telescoping into the next step in flow. The product stream containing crude 10 was mixed in-line with methyl-tertbutylether (MTBE) and saturated $NaHCO_3$ before phase separation using a hydrophobic, membrane-based separator (Zaiput) [40] (Scheme 3) to afford purified 10 in the organic phase. A loss of 5-10% of product to the water layer was observed, however this was deemed adequate as it prevented the need for a complete workup step in batch.

In the next step, 6 was reacted with hydroxylamine, which was facilitated by passing through a packed-bed of $K_2CO_3$ to give oxime 11 (Table 2). As was seen with the reaction to produce 6 (Table 1) reactant concentrations also had a dramatic effect on oxime formation. A series of experiments were conducted to optimize the continuous formation of 11. Reaction yields were modest at lower reactant concentrations across several temperatures and residence times (Table 2). Conversion to 11 increased when reactant concentrations were increased (9% at 0.1 M to 72% at 1 M) (Table 2, entries 1-6). Optimization of the flow rate with 1M concentrations of each reactant (Table 2, entries 6-8) showed that a flow rate of 1.0 ml $min^{-1}$ ($t_R$=20 min) was optimal, giving an isolated yield of 78% (Table 2, entry 7).

TABLE 2

Optimization of conversion of 6 to oxime 11

| Entry | Concentration[a] | Temp (° C.) | $t_R$ = min | Conv of 11 (%)[b] |
|---|---|---|---|---|
| 1 | 0.1M | 100 | 10 | 9 |
| 2 | 0.2M | 100 | 10 | 16 |
| 3 | 0.4M | 100 | 10 | 34 |
| 4 | 0.6M | 100 | 10 | 37 |
| 5 | 0.8M | 100 | 10 | 62 |
| 6 | 1.0M | 100 | 10 | 72 |
| 7 | 1.0M | 100 | 20 | 85 (78)[c] |
| 8 | 1.0M | 100 | 40 | 76 |

[a]Concentration of 10, 7 and hydroxylamine;
[b]conversion determined by GC-MS and $^1H$ NMR;
[c]Isolated yield The reductive amination of 11 performed in the first generation batch process was carried out using Raney Nickel at 80° C., 10 bar hydrogen pressure for 4-6 h [21-24]. In order to perform this step in a continuous fashion, a continuous stirred tank reactor [25, 41] was employed (Table 3). Materials were delivered to the CSTR vessel through an HPLC pump and reacted under hydrogen pressure with mechanical stirring. The dip tube in the CSTR was outfitted with a fritted metal filter, allowing for retention of the heterogeneous catalyst within the CSTR vessel. Optimization of this CSTR-based flow process (Table 3) showed near quantitative yields of 12 over a broad range of oxime 11 reactant concentrations. An optimum residence time was determined to be hours.

TABLE 3

Optimization of synthesis of 12

| Entry | Oxime [Concentration] | Temp (° C.) | Pressure (bar) | $t_R$ = hours | Conv of 12 (%)[a] |
|---|---|---|---|---|---|
| 1 | 0.05M | 80 | 10 | 4 | 94% |
| 2 | 0.25M | 80 | 10 | 4 | 96% |
| 3 | 0.5M | 80 | 10 | 4 | 97% |
| 4 | 2.0M | 80 | 10 | 4 | 98% (89%)[b] |
| 5 | 2.0M | 80 | 10 | 2 | 56% |
| 6 | 2.0M | 80 | 10 | 1 | 46% |

[a]conversion determined by GC-MS and $^1H$ NMR
[b]Isolated yield

Figure 8:
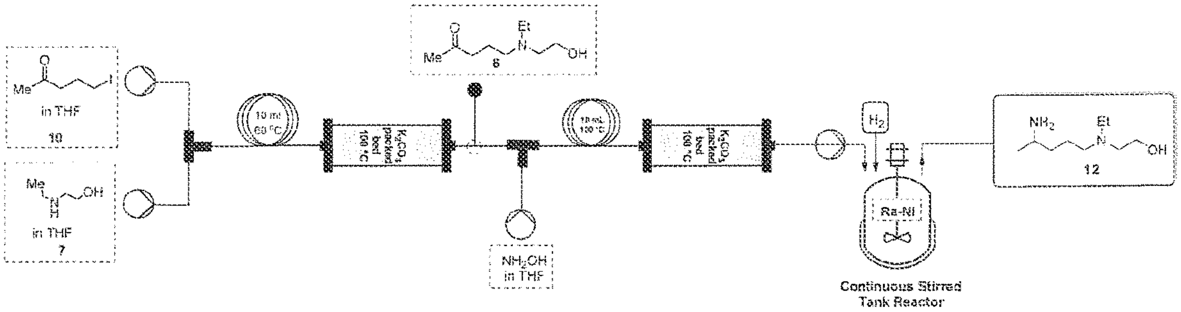
FIG. 8. Optimization of the flow process for synthesis of 12.

After optimizing the individual steps up to compound 12 the entire reaction was telescoped into a continuous reaction process that converts 10 and 6 into 12 (FIG. 8) with an overall isolated yield of 68% for compound 12.

With an optimized continuous process for producing the key intermediate 12, in-hand, reaction conditions for the conversion of 12 to HCQ were examined. In the commercial process this step is carried in batch under neat reactant conditions and requires a relatively long reaction time of 24-48 h [42-44]. In order to convert this step to a flow chemistry method, we employed a CSTR (Table 4). This final step, transforming 12 and 13 into 1, was first investigated in batch to optimize the conditions when implemented in an CSTR.

TABLE 4

Optimization of hydroxychoroquine 1

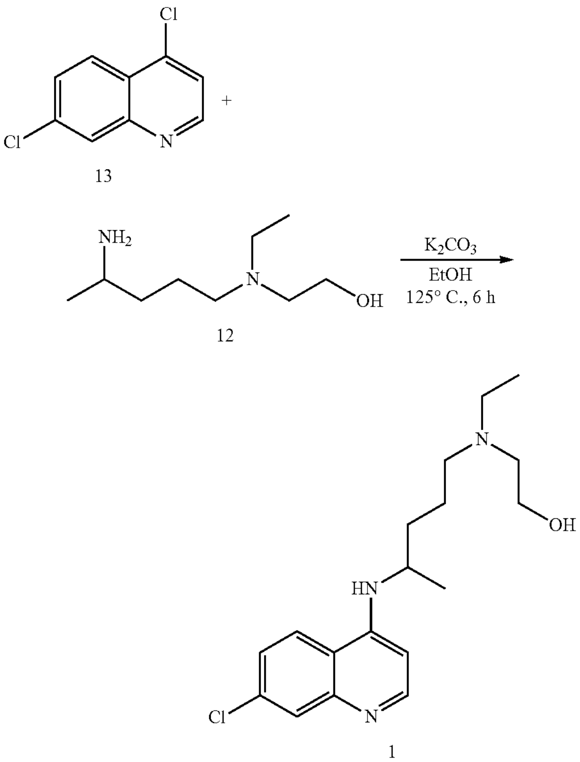

13
12
1

| Entry | Base | Solvent | Temp (° C.) | Conv. to 1 (%)[a] |
|---|---|---|---|---|
| 1 | NaOH | EtOH | 125 | 30 |
| 2 | KOH | EtOH | 125 | 35 |
| 3 | $K_2CO_3$ | EtOH | 125 | 82 |
| 4 | $Et_3N$ | EtOH | 125 | 61 |
| 5 | DIPEA | EtOH | 125 | 55 |
| 6 | $K_2CO_3/Et_3N$ | EtOH | 125 | 88 (78)[b] |

Reaction condition:
4,7-Dichloroquine 13 (1.0 equiv.), base (1.0 equiv.), amine 12 (1.2 equiv)
[a]conversion determined by HPLC and $^1H$ NMR
[b]Isolated yield Process optimization for the final step began by screening the effect of solvent and base(s) on HCQ yield. Screening of different polar-protic and non-protic solvents (see Table S-2 in SI) [45] demonstrated that ethanol is most effective for this transformation. During the screening of bases, the $pK_a$ of the amine and alcohol groups present in compound 12 were given careful consideration in order to minimize C—O bond formation (Table 4). NaOH or KOH in ethanol gave low (<40%) conversion, whereas using $K_2CO_3$ in ethanol gave 82% conversion to HCQ (Table 4, Entry 3). Attempts with organic bases (Entries 5-6) resulted in only moderate conversions to the desired product; however, using a 1:1 mixture of $K_2CO_3/Et_3N$ (1/1) in ethanol resulted in 88% conversion (Table 4, Entry 6) to 1, with corresponds to an isolated yield of 78%.

CONCLUSION

In summary, we have developed a high-yielding continuous flow process for the synthesis of hydroxychloroquine (HCQ) by optimizing continuous flow methods for the synthesis of key intermediates 6 and 12. Additionally we have developed and optimized flow chemistry conditions for performing reductive amination of 11 using Raney-Nickel as catalyst in a continuous stirring tank reactor (CSTR) for the synthesis of compound 12, and have incorporated it into a fully continuous telescoped process for synthesis of 12 from lactone 8 and aminoethanol 7. Feeding the output stream containing 12 from the above CSTR into a second CSTR in which 12 is converted to HCQ provides a completely continuous flow process from producing HCQ from readily available starting materials. This efficient process has the potential to increase global access to this strategically important antimalarial drug.

Optimization Reactions

All reactions for the preparation of substrates performed in standard, dry glassware under an inert atmosphere of nitrogen or argon unless otherwise described. All starting materials and reagents purchased from commercial sources and used as received unless otherwise noted. $^1H$ and $^{13}C$ NMR spectra recorded using 600 MHz spectrometers. Chemical shifts (δ) values given in ppm, and coupling constants (J) given in Hz. The 7.26 resonance of residual $CHCl_3$ (or 0 ppm of TMS) for proton spectra and the 77.23 ppm resonance of $CDCl_3$ for carbon spectra were used as internal references. Continuous flow experiments were carried out using the E-series flow reactor instrument purchased from Vapourtec Ltd. PFA tubing (1/16 OD×1 mm ID) was used for all reactor coils in flow experiments. Most of the reagents and starting materials were purchased from commercial sources and used as received. All HPLC chromatograms recorded on Agilent Technologies 1260 Infinity instrument with a Poroshell 120 EC-C18 column (4.6×50 mm, 2.7 micron). Continuous flow hydrogenation was performed using FlowCAT instrument.

Synthesis of 5-iodopentan-2-one (10)

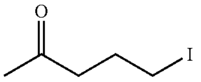
(10)

Two solutions, 2-Acetylbutyrolactone (8) (1.176 mL, 10.35 mmol, 1.0 equiv) and Hydroiodic acid (55% aqueous sol) were pumped at 1.0 $mLmin^{-1}$ using peristaltic pumps through a 10 mL coil (residence time, $t_R$=5 mins) at 80° C. The completion of the reaction was monitored using GC-MS. Complete consumption of starting material was observed. The reaction mixture was cooled to room temperature and sodium bicarbonate was added until neutralized at pH=7. The crude mixture was extracted with hexanes/MTBE and the combined organic phases were dried over anhydrous sodium sulfate and evaporated in vacuo to dryness yielding the desired product as a light brown liquid (14.72 g, 89%).

Figure 10:
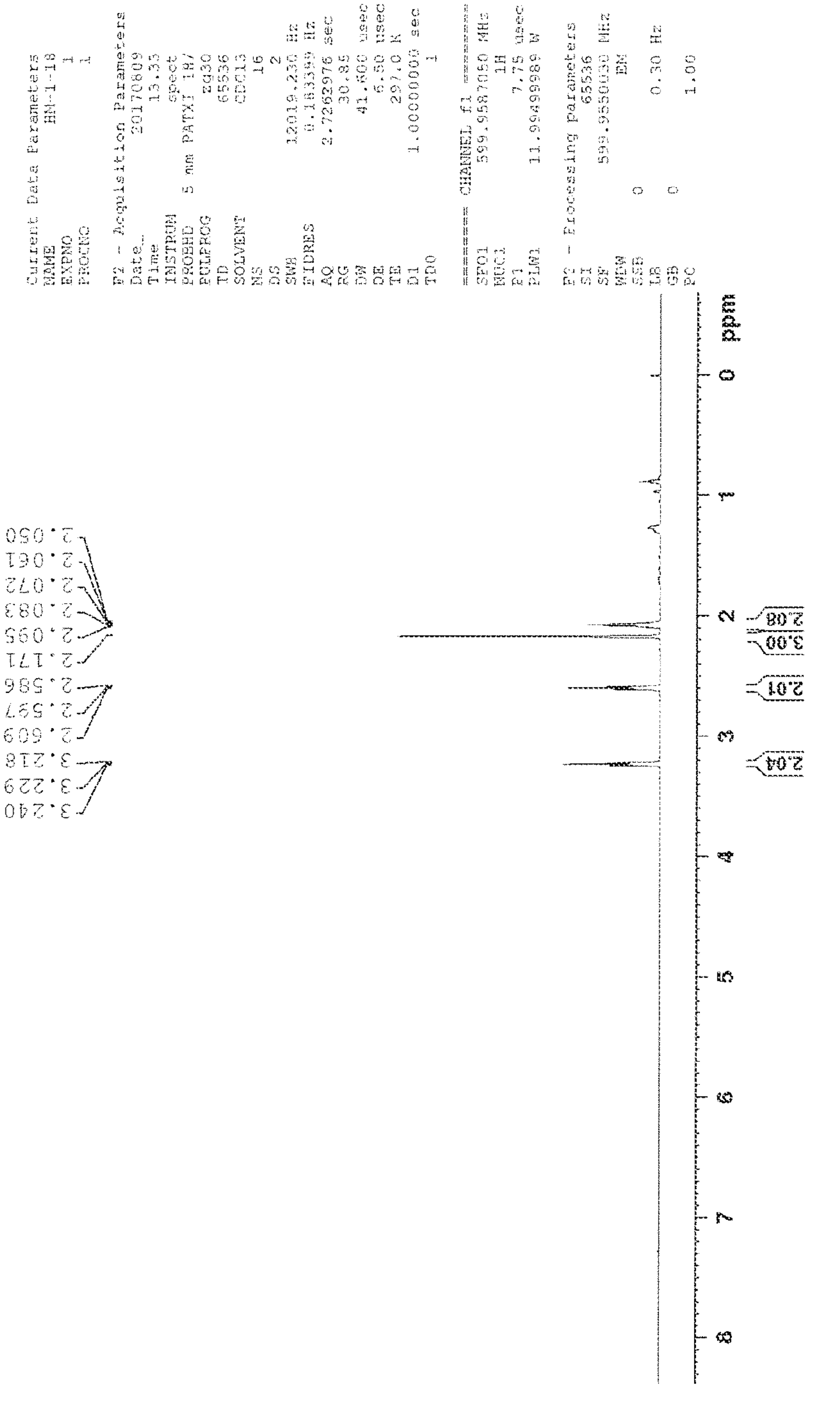
FIG. 10. $^{1}$H NMR Spectra of compound (10).
Figure 11:
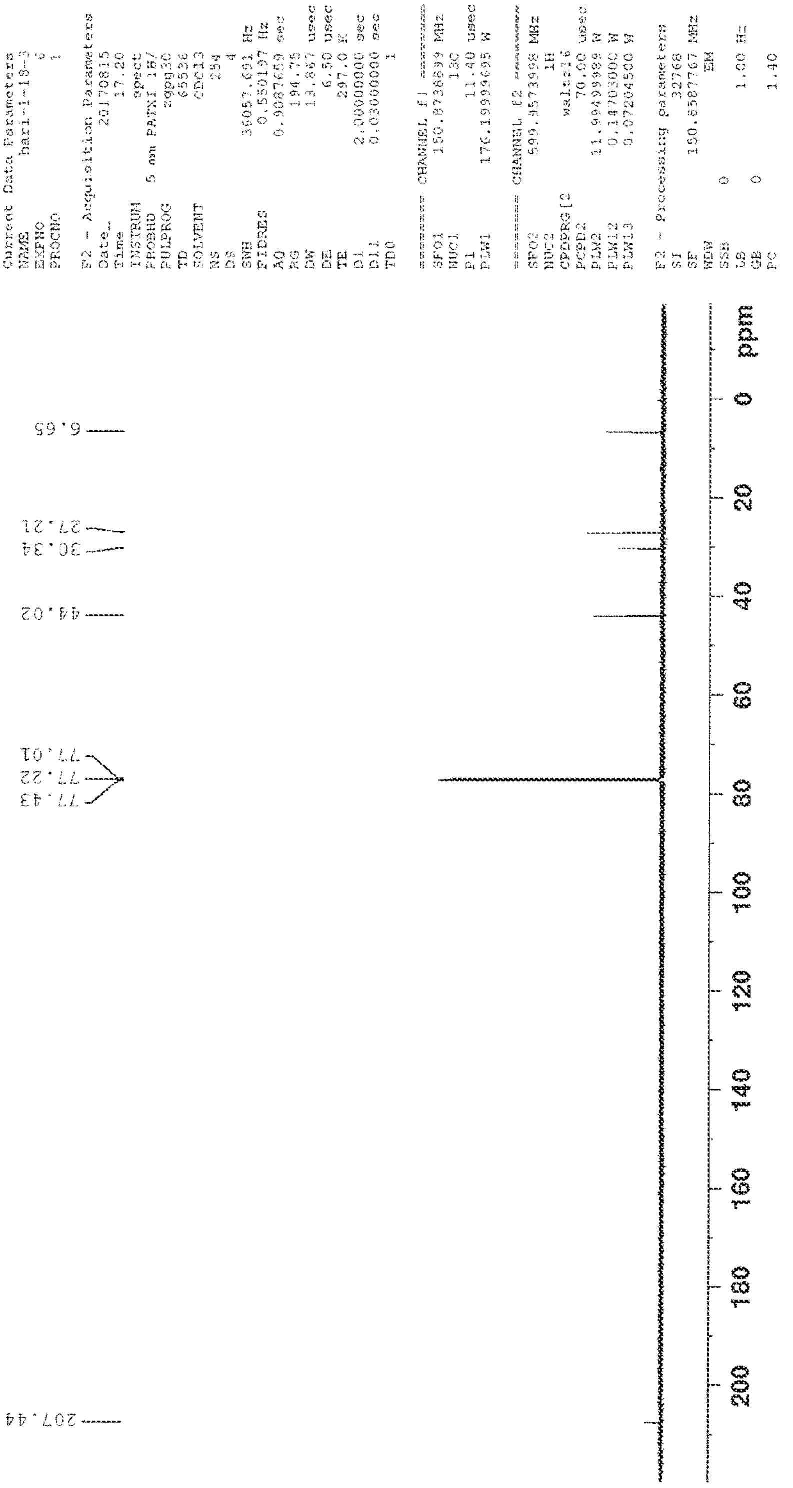
FIG. 11. $^{13}$C NMR Spectra of compound (10).

$^1H$ NMR (600 MHz, $CDCl_3$): δ 3.22 (t, J=6.9 Hz, 2H), 2.59 (t, J=6.9 Hz, 2H), 2.17 (s, 3H), 2.06 (quin, J=7.0 Hz, 2H); $^{13}C$ NMR (125 MHz, $CDCl_3$): δ 207.4, 44.0, 30.3, 27.2, 6.7; Spectra were obtained in accordance with those previously reported [3]; see FIG. 10 and FIG. 11.

Synthesis of 5-(ethyl(2-hydroxyethyl)amino)pentan-2-one (6)

(6)

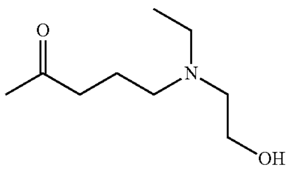

Telescope of compound 6: Prior to the state of the experiment, the flow reactor unit was rinsed with dry THF and flushed with nitrogen gas. At room temperature, the stock solutions of 5-iodopentan-2-one (10) (1.0 M) and 2-(ethylamino)ethan-1-ol (7) in THF solution (1.0 M) were streamed in at 0.5 $mLmin^{-1}$ via a T-piece into a 10 mL reactor coil ($t_R$=10 min) and passed through a packed bed reactor of potassium carbonate at 100° C. The output solution was collected and quenched with a saturated solution of ammonium chloride. The aqueous phase was extracted by DCM (3×50 mL) and the organic layers were combined, dried over sodium sulfate, and evaporated in vacuo to give a light brown liquid (14.05 g, 86%); $^1$H NMR (600 MHz, $CDCl_3$): δ 3.53 (t, J=5.2 Hz, 2H), 2.58 (m, 3H), 2.53 (m, 2H), 2.45 (t, J=6.7 Hz, 4H), 2.59 (t, J=6.9 Hz, 2H), 2.17 (s, 3H), 2.07 (quin, J=7.0 Hz, 2H); $^{13}$C NMR (125 MHz, $CDCl_3$): δ 208.9, 58.6, 55.0, 52.4, 47.2, 41.3, 30.0, 21.2, 11.7;

Spectra were obtained in accordance with those previously reported [38, 39].

Synthesis of (E)-5-(ethyl(2-hydroxyethyl)amino) pentan-2-one oxime (11)

(11)

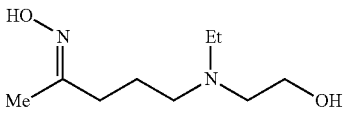

Flow: Prior to the start of the experiment, the flow reactor unit was rinsed with dry THF and flushed with nitrogen gas. At room temperature, the stock solutions of 5-iodopentan-2-one (10) (1.0 M) and 2-(ethylamino)ethan-1-ol (7) in THF solution (1.0 M) were streamed in at 0.5 $mLmin^{-1}$ via a T-piece into a 10 mL reactor coil ($t_R$=10 min) and passed through a packed bed reactor of potassium carbonate. The output solution was streamlined with hydroxylamine (1.0 M) at 1.0 $mLmin^{-1}$ via a T-piece into a 10 mL reactor coil ($t_R$=10 min) and passed through a packed bed reactor of potassium carbonate at 100° C. The reaction mixture was then concentrated in vacuo, taken up in dichloromethane (3×20 mL) and concentrated under reduced pressure to yield 11 as light brown liquid. The crude product was used in the next step without further purification.

Synthesis of 2-((4-aminopentyl)(ethyl)amino)ethan-1-ol (12)

(12)

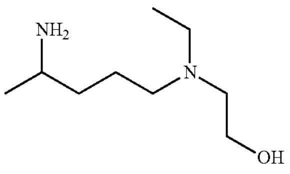

Flow: The synthesis of compound 12 was performed in a HEL continuous stirred tank reactor (CSTR) with a reaction volume of 150 mL. The reaction vessel was first charged with Raney Nickel (1.0 g). The Raney Nickel catalyst was retained in the CSTR by the 2 μm metal filter frit on the diptube of the exit stream. The reaction mixture, consisting of compound 11 (0.05-2.0 M) in THE was pumped by an HPLC pump set at a flow rate of 0.6-2.5 $mLmin^{-1}$ into the reaction vessel. The reaction pressure was set to 10 bar of hydrogen supplied by hydrogen gas (ultra high purity) at a flow rate of 0.5 $mLmin^{-1}$. The reaction temperature was set to 80° C. which was controlled by a thermocouple positioned in the reaction mixture. The reaction was stirred with mechanical stirring (750 rpm) to provide proper mixing. Two thermocouples were used to control the reaction volume in the reactor by setting a level control of −3° C. The lower thermocouple constantly measured and controlled the reaction temperature and the upper thermocouple measured the temperature at approximately 150 mL reactor volume. When the two thermocouples were within 3° C., the level control ‘opened’ the exit stream diptube to allow products to exit the reactor, or ‘closed’ the exit stream diptube to allow the reactor to till when the temperature difference between the two thermocouples was greater than 3° C. Product was collected after a full reaction volume of material (150 mL) had passed through the CSTR indicating that steady-state was reached. The reaction was monitored by liquid chromatography and $^1$H NMR. The reaction mixture was filtered through a celite pad and dried under reduced pressure. The solution was extracted with water (10 mL) and dichloromethane (3×20 mL). The organic layers were combined, washed with brine and dried over sodium sulfate and evaporated in vacuo. The resulting oil was fractionally distilled to give a colorless liquid (16.83 g, 84%). $^1$H NMR (600 MHz, $CDCl_3$): δ 3.53 (t, J=5.3 Hz, 2H), 2.89 (sx, J=6.4 Hz, 1H), 2.57 (t, J=5.5 Hz, 2H), 2.55 (t, J=7.0 Hz, 2H), 2.45 (t, J=7.0 Hz, 2H), 1.55-1.44 (m, 2H), 1.36-1.27 (m, 2H), 1.22 (t, J=7.1 Hz, 2H), 1.07 (d, J=7.1 Hz, 2H), 1.00 (t, J=7.1 Hz, 2H); $^{13}$C NMR (125 MHz, $CDCl_3$): δ58.2, 54.9, 53.2, 46.9, 46.7, 36.6, 23.8, 22.4, 10.6; Spectra were obtained in accordance with those previously reported [38, 39].

Synthesis of 2-((4-((7-chloroquinolin-4-yl)amino) pentyl)(ethyl)amino)ethan-1-ol (1)

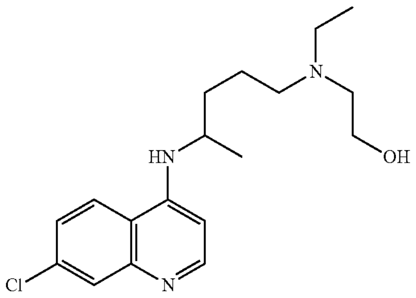 [SMILES: CCN(CCO)CCCC(C)Nc1ccnc2cc(Cl)ccc12]

Batch: In a CSTR reactor, 4,7-Dichloroquinoline (200 mg, 1.0 mmol), compound (12) (208 mg, 1.2 mmol), triethylamine (0.069 mL, 0.5 mmol, 0.5 equiv) and potassium carbonate (69 mg, 0.5 mmol, 0.5 equiv) were combined and to this mixture was added ethanol (1.0 mL). The ethanol was distilled off from the reaction mixture and kept under nitrogen atmosphere (15 psi). The reaction was left at 125° C. in the nitrogen atmosphere for 6 h. After cooling, the mixture was transferred into a separatory funnel using 1M aqueous sodium hydroxide (5 mL) and dichloromethane (2×20 mL). The organic phases were separated and the aqueous phase was re-extracted with dichloromethane (2×10 mL). The organic layers were combined and dried over sodium sulfate and evaporated in vacuo. The crude material was purified using flash chromatography with DCM:$Et_3N$: MeOH (95:3:2) to give a white solid (0.263 g, 78%). $^1H$ NMR (600 MHz, $CDCl_3$): δ 8.48 (d, J=5.4 Hz, 1H), 7.93 (d, J=5.4 Hz, 1H), 7.70 (d, J=9.2 Hz, 1H), 7.34 (dd, J=8.8, 7.3 Hz, 1H), 6.39 (d, J=5.4 Hz, 1H), 4.96 (d, J=7.5 Hz, 1H), 3.70 (sx, J=6.8 Hz, 1H), 3.55 (m, 2H), 2.57 (m, 5H), 2.49 (m, 2H), 1.74-1.62 (m, 1H), 1.65-1.53 (m, 3H), 1.31 (d, J=6.9 Hz, 3H), 1.24 (d, J=7.2 Hz, 2H); $^{13}C$ NMR (125 MHz, $CDCl_3$): δ152.2, 149.5, 149.2, 135.0, 129.0, 125.4, 121.2, 117.4, 99.4, 58.6, 54.9, 53.18, 48.5, 47.9, 34.5, 24.1, 20.6, 11.9;

Spectra were obtained in accordance with those previously reported [38, 39].

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for synthesizing hydroxychloroquine (HCQ), comprising in a flow reactor, i) reacting 5-iodopentan-2-one with 2-(ethylamino) ethan-1-ol to form 5-(ethyl(2-hydroxyethyl)amino) pentan-2-one; and ii) converting 5-(ethyl(2-hydroxyethyl)amino)pentan-2-one to (E)-5-(ethyl(2-hydroxyethyl)amino)pentan-2-one oxime;

and in a first continuous stirred tank reactor (CSTR)

iii) contacting (E)-5-(ethyl(2-hydroxyethyl)amino)pentan-2-one oxime with a catalyst to form 5-(ethyl(2-hydroxyethyl)amino)-2-aminopentane;

and in a second CSTR, iv) reacting the 5-(ethyl(2-hydroxyethyl)amino)-2-aminopentane with 4,7,-dichloroquinoline in the presence of a base to form HCQ.

2. The method of claim 1, wherein steps i), ii) and iii) are conducted in a solvent that is the same for each step.

3. The method of claim 2, wherein the solvent is tetrahydrofuran (THF).

4. The method of claim 1, wherein reacting step iv) is performed in an alcohol.

5. The method of claim 4, wherein the alcohol is ethanol.

6. The method of claim 1, wherein the base is $K_2CO_3$/$Et_3N$.

7. The method of claim 1, wherein reacting step iv) proceeds for 6 hours.

8. The method of claim 1, wherein the 5-iodopentan-2-one is formed by a) reacting α-acetyl butyrolactone with an iodine donor in an aqueous solvent.

9. The method of claim 8, further comprising a step of b) extracting the 5-iodopentan-2-one from the aqueous solvent with an organic solvent.

10. The method of claim 9, wherein the steps of a) reacting and b) extracting are performed in line in a first flow reactor.

11. The method of claim 10, wherein the first flow reactor is in line with the flow reactor of claim 1.

12. The method of claim 8, wherein the iodine donor is hydroiodic (HI) acid.

13. The method of claim 8, wherein the α-acetyl butyrolactone is neat.

14. The method of claim 9, wherein the step of extracting is performed using a hydrophobic, membrane-based separator.

15. The method of claim 1, wherein the catalyst is a Raney nickel catalyst.

16. A system for synthesizing hydroxychloroquine (HCQ), comprising a first heated reactor coil configured to receive 5-iodopentan-2-one and 2-(ethylamino)ethan-1-ol and output 5-(ethyl(2-hydroxyethyl)amino)pentan-2-one;

a first packed bed reactor comprising a neutralizing agent and configured to receive 5-(ethyl(2-hydroxyethyl)amino)pentan-2-one from the first heated reactor and output neutralized 5-(ethyl(2-hydroxyethyl)amino)pentan-2-one;

a second heated reactor coil configured to receive neutralized 5-(ethyl(2-hydroxyethyl)amino) pentan-2-one from the first packed bed reactor, receive hydroxylamine, and output (E)-5-(ethyl(2-hydroxyethyl)amino)pentan-2-one oxime;

a second packed bed reactor comprising a neutralizing agent and configured to receive 5-(ethyl(2-hydroxyethyl)amino)pentan-2-one oxime from the second heated reactor coil, and output neutralized (E)-5-(ethyl(2-hydroxyethyl)amino) pentan-2-one oxime;

a first continuous stirred tank reactor (CSTR) configured to contain a catalyst, receive neutralized (E)-5-(ethyl(2-hydroxyethyl) amino) pentan-2-one oxime from the second packed bed reactor, and output 5-(ethyl(2-hydroxyethyl)amino)-2-aminopentane;

and a second CSTR configured to receive 5-(ethyl(2-hydroxyethyl)amino)-2-aminopentane from the first CSTR, receive 4,7,-dichloroquinoline, and output HCQ.

17. The system of claim 16, wherein the system further comprises a heated reaction coil configured to receive α-acetyl butyrolactone and receive an iodine donor, and output 5-iodopentan-2-one, a reaction coil configured to receive 5-iodopentan-2-one from the heated reaction coil, and receive a base and a hydrophobic, membrane-based separator configured to receive 5-iodopentan-2-one from the unheated reaction coil extract 5-iodopentan-2-one from the aqueous solvent with an organic solvent, and output 5-iodopentan-2-one in an organic phase.

18. The system of claim 16, wherein the first heated reactor coil receives the 5-iodopentan-2-one in an organic phase from the hydrophobic, membrane-based separator.

19. The system of claim 16, wherein the catalyst is a Raney nickel catalyst.

* * * * *